United States Patent [19]

Panster et al.

[11] Patent Number: 5,380,791

[45] Date of Patent: Jan. 10, 1995

[54] METHOD OF PRODUCING SULFONATED ORGANOSILICON COMPOUNDS AND CORESPONDING AQUEOUS SOLUTIONS

[75] Inventors: Peter Panster, Rodenbach; Arno Jaenes, Hasselroth; Thomas Goebel, Hanau, all of Germany

[73] Assignee: Degussa Aktiengesellschaft, Frankfurt am Main, Germany

[21] Appl. No.: 993,009

[22] Filed: Dec. 18, 1992

[30] Foreign Application Priority Data

Dec. 20, 1991 [DE] Germany .................... 4142129

[51] Int. Cl.$^6$ ............................................ C08L 83/00
[52] U.S. Cl. ................................. 524/837; 524/858; 524/863; 528/9; 528/30
[58] Field of Search .............. 528/9, 30; 524/837, 524/858, 863

[56] References Cited

U.S. PATENT DOCUMENTS

| | | | |
|---|---|---|---|
| 4,267,213 | 5/1981 | Beck et al. | 427/292 |
| 4,362,885 | 12/1982 | Panster et al. | 556/446 |
| 4,410,669 | 10/1983 | Panster et al. | 525/474 |
| 4,424,332 | 1/1984 | Panster et al. | 528/30 |
| 4,455,415 | 6/1989 | Panster et al. | 528/39 |
| 4,552,700 | 11/1985 | Panster et al. | 556/9 |
| 4,595,740 | 6/1986 | Panster | 528/30 |
| 4,645,847 | 2/1987 | Panster et al. | 556/9 |
| 4,645,848 | 2/1987 | Panster et al. | 556/9 |
| 4,647,644 | 3/1987 | Panster et al. | 528/30 |
| 4,647,679 | 3/1987 | Panster et al. | 556/9 |
| 4,647,682 | 3/1987 | Panster et al. | 556/431 |
| 4,758,277 | 7/1988 | Spruegel et al. | 106/36 |
| 4,772,457 | 9/1988 | Panster et al. | 423/561 R |
| 4,845,163 | 7/1989 | Panster et al. | 525/475 |
| 4,855,470 | 8/1989 | Panster et al. | 556/421 |
| 4,954,599 | 9/1990 | Panster et al. | 528/38 |
| 4,999,413 | 3/1991 | Panster et al. | 528/30 |
| 5,003,024 | 3/1991 | Panster et al. | 528/30 |
| 5,019,637 | 5/1991 | Panster et al. | 528/25 |
| 5,061,773 | 10/1991 | Panster et al. | 528/9 |
| 5,093,451 | 3/1992 | Panster et al. | 528/9 |
| 5,094,831 | 3/1992 | Klockner et al. | 423/342 |
| 5,126,473 | 6/1992 | Klockner et al. | 556/473 |
| 5,130,396 | 7/1992 | Panster et al. | 528/9 |
| 5,132,337 | 7/1992 | Panster et al. | 523/117 |
| 5,187,134 | 2/1993 | Panster et al. | 502/158 |

FOREIGN PATENT DOCUMENTS

| | | |
|---|---|---|
| 0098946 | 2/1984 | European Pat. Off. |
| 2139097 | 1/1973 | France . |
| 2422672 | 11/1979 | France . |
| 3226093 | 1/1984 | Germany . |
| 3808174 | 3/1988 | Germany . |
| 1005872 | 10/1961 | United Kingdom . |
| 1030888 | 5/1966 | United Kingdom . |
| 1198096 | 7/1970 | United Kingdom . |
| 1270977 | 4/1972 | United Kingdom . |
| 1358350 | 7/1974 | United Kingdom . |

OTHER PUBLICATIONS

"Novel Solid-Acid Catalysts-Poly (Organosiloxanes) Bearing Sulfo Groups", from Acid-Base Catal. Proc. Int. Symp., 1988, pp. 379–396, edited by K. Tanabe, authors: Y. Ono and S. Suzuki.

Chemical Abstracts, vol. 82, 1975, Abstract No. 43503b.

*Primary Examiner*—Melvyn I. Marquis
*Assistant Examiner*—Karen A. Dean
*Attorney, Agent, or Firm*—Beveridge, DeGrandi, Weilacher & Young

[57] ABSTRACT

A method of producing 0.01 to 70 wt. % aqueous solutions of sulfonated organosilicon compounds having the formula $$[(HO)_3Si\text{-}R^1\text{-}SO_3^-]_xM^{x+} \quad (I)$$

or oligomeric siloxane derivatives thereof, condensed via oxygen bridges. The solution optionally also contains compounds of formula (III) e.g., Si(OH)$_4$ or Al(OH)$_3$, or the like, or derivatives thereof condensed via oxygen bridges. The ratio of Si atoms of formula (I) to the sum of Si and/or Al atoms of formula (III) is 1:0 to 1:3, and the total concentration of compounds (I)+(III) is 0.01 to 70 wt. %. The starting material for the method is a polymeric di-, tri-, or tetrasulfane compound made up of units having the formula:

(Abstract continued on next page.)

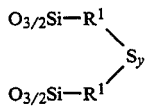

wherein $R^1$ has the same meaning as in formula (I), and $y=2$, 3 or 4. The starting material of formula (IV) is suspended in water. The suspension is mixed at 10° to 100° C. with hydrogen peroxide and is then agitated at 30° to 150° C. until a substantially clear solution is obtained. The solution is cooled and optionally neutralized, freed from any remaining insoluble components, washed and then adjusted to the required concentration.

17 Claims, No Drawings

METHOD OF PRODUCING SULFONATED ORGANOSILICON COMPOUNDS AND CORESPONDING AQUEOUS SOLUTIONS

BACKGROUND OF THE INVENTION

The invention relates to aqueous solutions of sulfonated organosilicon compounds for use as starting materials, for example, for insoluble acid catalysts or for surface modification of inorganic materials. The novel method is characterized in that it is extremely economic and ecological, and it also can be used to produce aqueous solutions which contain no organic product apart from the sulfonated active component.

Sulfonated organosilicon compounds in insoluble form, as described in German Patent Application No. DE 32 26 093, are used more particularly as ion exchangers and solid acid catalysts (see also Acid-Base Catal., Proc. Int. Symp., 1988, pp. 379–396, edited by K. Tanabe, Tokyo, authors Y. Ono and S. Suzuki). These documents are entirely incorporated herein by reference.

In soluble form, preferably in aqueous solutions, these compounds are used as emulsifiers for reducing the surface tension of aqueous media or for surface modification of inorganic phases, for example, for producing chromatography phases.

The literature describes various methods of producing soluble sulfonated organosilicon compounds, silanes and siloxanes. For example, Great Britain Patent Application Nos. GB 1,270,977 and GB 1,198,096 describe the manufacture of sulfonated organosilicon compounds by reacting the corresponding epoxidized silane or siloxane with an amine sulfonate or with sodium bisulfite. These documents are entirely incorporated herein by reference. British Patent Application No. 1,005,872 (which is also entirely incorporated herein by reference) describes the manufacture of sulfonated organosilicon compounds obtained by reacting the corresponding unsaturated organosilicon compounds with an alkali metal bisulfite or an alkali metal pyrosulfite. In the case of British Patent Application No. 1,030,888, a mercaptoethyl silicon compound is reacted with sodium ethoxide and then with a hydroxypropane sulfonic acid. In German Patent Application No. DE-OS 38 08 174, organosilanes and organosiloxanes containing sulfone groups are obtained by oxidation of the corresponding mercaptopropyl-substituted starting compounds with sodium permanganate. These documents also are entirely incorporated herein by reference.

These known methods however have various disadvantages. The required reactants are either expensive or difficult to obtain. In the method of GB 1 005 872, the reaction has to be carried out under high pressure. In the case of DE-OS 38 08 174, manganese oxide occurs as a byproduct, and it is expensive to remove and dispose of.

BRIEF DESCRIPTION OF THE INVENTION

The method in accordance with the invention seeks to overcome these and other disadvantages in providing a method for producing sulfonic organosilicon compounds and their corresponding aqueous solutions.

The invention relates to a method of producing soluble sulfonated organosilicon compounds and the corresponding aqueous solutions, wherein the products are manufactured economically and in an ecologically efficient manner in water containing no additional organic components.

The end products obtained by the method in accordance with the invention, apart from the sulfonated organosilicon active component, contain only water as the solvent. No additional organic components, such as alcohol, are included. In the method according to the invention, an organopolysiloxane containing disulfane, trisulfane or tetrasulfane groups is oxidized with $H_2O_2$ or inorganic or organic peracids or hypobromite. These polysiloxanes are described in German Patent Application No. 32 26 091 (which is entirely incorporated herein by reference). The oxidation of these polymeric silicon compounds with $H_2O_2$ has been described in German Patent Application No. 32 26 093, but the products obtained are only insoluble polysiloxanes containing sulfonate groups and having a stoichiometrically undefined composition.

It has now been found that the oxidation process can result practically quantitatively in soluble sulfonated organosilicon compounds with a defined stoichiometric composition, if the reaction conditions according to the invention are maintained.

DETAILED DESCRIPTION OF THE INVENTION

The invention relates to a method of producing 0.01 to 70% by weight aqueous solutions of sulfonated organosilicon compounds having the formula:

$$[(HO)_3Si\text{-}R^1\text{-}SO_3^-]_xM^{x+} \quad (I)$$

or oligomeric siloxane derivatives thereof condensed via oxygen bridges. In formula (I), $R^1$ denotes a straight-chain or branched alkylene group with 1 to 12 carbon atoms; a cycloalkylene group with 5 to 8 carbon atoms; or a unit having the formula:

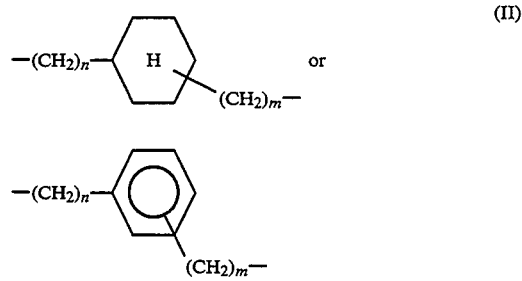

(II)

in which n or m is a number from 0 to 6 and denotes the number of methylene groups on the silicon or sulfur atom. Further, in formula (I), M denotes $H^+$, or optionally also $NH_4^+$ or a metal ion having a valence of $x=1$ to 4. The solution optionally also contains compounds having the formula:

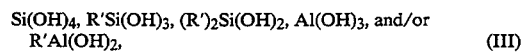

$$Si(OH)_4, R'Si(OH)_3, (R')_2Si(OH)_2, Al(OH)_3, \text{and/or } R'Al(OH)_2, \quad (III)$$

or derivatives thereof condensed via oxygen bridges. In formula (III), R' denotes a methyl or ethyl group.

The ratio of Si atoms from units of formula (I) to the sum of the Si and/or Al atoms from units of formula (III) is 1:0 to 1:3, and the total concentration of the compounds of formula (I) and formula (III) is 0.01 to 70 wt. %.

The invention is characterized in that a polymeric disulfane, trisulfane, or tetrasulfane compound made up of units having the formula:

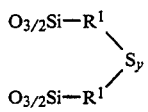 (IV)

in which $R^1$ in the two cases can be the same or different and has the same meaning as in formula (I). In formula (IV), y is 2, 3 or 4, and the free valences of the oxygen atoms bonded to the silicon atom are saturated by the silicon atoms in other formula (IV) groups and/or by the metal atom/oxygen groups in the cross-linking bridge members:

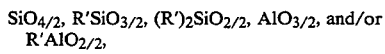 (V)

in which R', as in formula (III), denotes a methyl or ethyl group. The ratio of Si atoms from formula (IV) units to the sum of the Si and/or Al atoms from formula (V) units is 1:0 to 1:3. The compound of formula (IV) is suspended in a concentration of 0.1 to 50 wt. % in water. The suspension is mixed at a temperature in the range of 10° to 100° C. for a time in the range of 2 to 20 hours with the stoichiometrically required or an excess quantity of hydrogen peroxide, relative to the formula (IV) units. The hydrogen peroxide is in the form of a 1 to 70 wt. % solution. After this mixing, the suspension is agitated at a temperature in the range of 30° to 100° C. for up to 60 hours and at a temperature in the range of 100° to 150° C. for up to a further 60 hours at normal pressure or optionally at an excess pressure equal to the sum of the partial pressures of the components of the mixture at the respective temperature.

The agitation continues until a substantially clear solution is obtained and any excess hydrogen peroxide has decomposed. At this time, the solution is cooled and optionally mixed with ammonia, an amine, a water-soluble metal oxide, a water-soluble metal hydroxide, a water-soluble metal hydrogen carbonate, a water-soluble carbonate, or aqueous solutions thereof in order to neutralize the substantially quantitatively-formed sulfonate of formula (I) and any sulfuric acid present. Any small proportions of insoluble constituents may then be separated by filtering or centrifuging. The residue is washed with water, and the solution of product combined with the washing liquor is adjusted to the required concentration of the sulfonated organosilicon compound in the aforementioned range of 0.01 to 70 wt. %, for example, by adding water or removal of water by distillation.

With regard to this process, it has surprisingly been found that the reaction is quantitative, i.e., in the case of disulfane, it is in accordance with the equation:

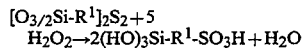 (1)

In other words, there are no side-reactions involving oxidative decomposition of the hydrocarbon groups or the carbon/silicon skeleton. Another surprising fact is the substantially quantitative yield on oxidation with $H_2O_2$ and the complete conversion of the insoluble disulfane group-containing polysiloxane compound according to formula (IV) into a soluble product as per formula (I).

The solubility of the sulfonate as per formula (I) appears to be assisted by the fact that, during oxidation of the disulfane group, a very high density of similarly charged sulfonate groups would occur on the siloxane skeleton if it were not that the repulsion of these negative charges caused the always-present reaction equilibrium

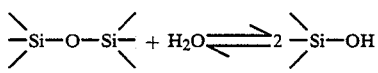 (2)

to be shifted substantially to the right. In the process, hydrolysis of the polysiloxane skeleton occurs and soluble organosilanetriol units are formed from the insoluble highly cross-linked siloxane matrix.

As is known, the formula (I) units, depending on their concentration in aqueous solution, can also be in the form of soluble oligomers in which at least two molecules are linked via a siloxane bridge. When the concentration of an aqueous solution of formula (I) compounds increases above the critical barrier of 70 wt. %, higher-molecular structures are apparently formed and deposited as solids from the solution. This process however is reversible by adding water, so that, in principle, in some applications of these sulfonated organosilicon compounds, a corresponding suspension also can be used.

The marked tendency of sulfonated organosilicon compounds to form soluble monomeric compounds as per formula (I) or siloxane derivatives thereof, condensed via oxygen bridges, is also shown by the fact that, in addition to the formula (I) compounds, non-organofunctional compounds having the formula (III) can also be present in solution and can independently and spontaneously form an insoluble network. Owing however to the presence of sulfonated organosilicon compounds, up to 3 units of formula (III) per unit of formula (I) can be held in solution. It is only when the ratio is higher that polymeric products of compounds of formula (III) precipitate out of these solutions.

Oligomeric derivatives, i.e., condensed derivatives, present in solution in equilibrium with the corresponding monomers, in dependence, for example, on the concentration, acid content and temperature, can have inter alia the following structure:

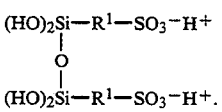

In the presence of a dissolved formula (III) compound, the following mixed oligomeric structures also presumably occur:

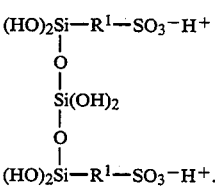

The stoichiometric quantity of hydrogen peroxide relative to units of formula (IV) is necessary to obtain quantitative conversion of all disulfane, trisulfane, or tetrasulfane groups each into two sulfonate groups and optional sulfate groups. If the amount of H₂O₂ is insufficient or if the reaction conditions are wrong, an insoluble residue will remain after all the H₂O₂ has been used up. To accelerate the reaction, in individual cases, an up to 10% molar excess of H₂O₂ can be used without adversely affecting the yield of the product. Larger excesses, however, often result in side-reactions or leave hydrogen peroxide in the final sulfonate-containing solution. The peroxide has to be removed separately, for example, by a decomposition catalyst, by boiling or by a chemical reaction.

One particularly advantageous form of the process in accordance with the invention uses a starting material which is readily available industrially, such as, polymeric disulfane, trisulfane, or tetrasulfane compounds having units having the formula:

in which y is 2, 3 or 4 and, as before, the free valences of the oxygen atoms bonded to the silicon atom are saturated by the silicon atoms in other formula (VI) groups, and/or by metal atom/oxygen groups in the cross-linking bridge members (V). The ratio of Si atoms in formula (VI) units to the sum of the Si and/or Al atoms in formula (V) units is 1:0 to 1:3. In this method, aqueous solutions of sulfonated organosilicon compounds having the formula:

$$[(HO)_3Si\text{-}(CH_2)_3\text{-}SO_3^-]_xM^{x+} \qquad (VII)$$

or condensed derivatives thereof in solution are obtained. In formula (VII), M denotes H⁺ or optionally NH₄⁺ or a metal ion having a valence of x=1 to 4. The solution also contains dissolved formula (III) compounds or condensed oligomeric derivatives thereof, the ratio of Si atoms in units of formula (VII) to the sum of the Si and/or Al atoms in units of formula (III) is 1:0 to 1:3.

Of course, when trisulfanes or tetrasulfanes are used, one or two moles of free sulfuric acid are first formed during oxidation, and can optionally be neutralized as described. A corresponding extra quantity of H₂O₂ is also needed. If this free sulfuric acid or the resulting sulfates cause trouble during use of the sulfate solution, in a preferred form of the invention the starting material is a polymeric disulfane having the formula:

in which R¹ has the same meaning as in formula (IV) and the free valences of the oxygen atoms bonded to the silicon atom are saturated by the silicon atoms in other formula (IV) groups and/or by cross-linking formula (V) bridge components.

Among these disulfanes, the preferred starting material for the sulfonate solution is the disulfane having the formula:

because of its industrial availability.

The water in which the polysiloxane sulfane for oxidation is suspended preferably has a pH in the range of 3 to 9.

In individual cases, however, the pH can be made higher or lower. But, if the pH is higher, H₂O₂ may decompose, whereas if the pH is lower, oxidation is slower. The pH can also be kept constant in the range from 3 to 9 during oxidation, if the sulfonate formed is continuously neutralized with amine; ammonia; water-soluble metal oxide; water-soluble metal hydroxide; water-soluble metal hydrogen carbonate; water-soluble metal carbonate; or aqueous solutions thereof, so that the solution obtained at the end of oxidation is a sulfonate having the formula (I), but in which M does not stand for H. This method can be followed if oxidation occurs too slowly in the sulfonic acid solution as it forms. Slow oxidation is advantageous, however, in that no undesired byproducts occur.

The total concentration of the units of formula (IV) starting material in water can be in the range of 0.1 to 50 wt. %. With a view, however, to a high space/time yield, it is desirable to have a maximum concentration, limited upwardly by the capacity of the suspension to be agitated and the exothermic nature of the reaction. The starting concentration of 10 to 35% by weight has been found to be a particularly advantageous range, i.e., a compromise taking account of all aspects. Oxidation is preferably brought about with about 35 wt. % hydrogen peroxide, available on a large industrial scale. The choice of concentration is also dependent on the same considerations as in the case of the concentration of solids, and also on selectivity aspects.

In a preferred variant of the invention, the quantity of hydrogen peroxide used for oxidation can be in a stoichiometric excess of up to 10 mol % relative to the conversion of all the sulfur atoms in the starting polysiloxane into sulfonate or optionally sulfonate units.

The temperature range of 10°–100° C. at which hydrogen peroxide is added is advantageous in that it avoids a too slow reaction and also a too fast uncontrolled reaction resulting in decomposition of H₂O₂. In principle, the temperature must be above a minimum, so that the reaction is completed during the addition of H₂O₂. A temperature range of 40° to 80° C. has been found serviceable. After a short heating-up, this range can be efficiently maintained via the rate of addition and the intensity of cooling, which is necessary since the reaction is exothermic. The subsequent reaction slowly becomes less exothermic, and external energy has to be supplied at the end. The final reaction, lasting up to 60 hours at 30° to 150° C., serves to complete the process and destroy excessive hydrogen peroxide. The process is usually operated at normal pressure, and preferably at the reflux temperature.

If no bases are used during oxidation, the main substance obtained as per equation (1) is the free sulfonate, which can be used without additional chemical treatment, optionally after filtration and/or concentration or dilution.

A liquid, solid or gaseous inorganic or organic acid can also be dissolved in the sulfonate-containing solution, if required by the special use to which the solution is put.

In the event of partial or complete neutralization, the base, which is present in gaseous, liquid or solid form, can be added at one time or in batches, allowing for the evolution of heat during neutralization. If the sulfonate solution needs to be made basic, an excess of base can be added.

The insoluble constituents, small quantities of which remain in the sulfonate solution after oxidation, are mainly impurities which frequently occur in the starting polysiloxane as per formula (IV). These insoluble solids are easy to remove by conventional methods of filtration or centrifuging. The solution obtained, for example, after filtration, may alternatively be concentrated in vacuo.

$H_2O_2$ is particularly preferred as the oxidizing agent, because of its eco-friendly character. However hydrogen peroxide can be replaced, in principle, by related per-compounds, such as organic peracids, peroxomonosulfates, peroxodisulfates, peroxomonosulfuric acid, peroxodisulfuric acid, bromine water (hypobromite), or the like, optionally formed in situ.

The polymeric disulfane compound according to formula (IV) can also be formed indirectly in situ in a one-pot reaction before oxidation, by hydrolysis and concentration of a suitable monomer as per DE-PS 32 26 091. The compound can then be washed with water to remove by-products resulting from manufacture and can then be oxidized when wet or at least without drying. The alcohol liberated in the process can be removed, after which the method according to the invention is continued.

In the case where trisulfanes or tetrasulfanes having the formula (IV) or (VI) are used as the starting material, the free sulfuric acid formed during oxidation can also be separated in the form of a difficultly-soluble sulfate from the aqueous solution containing the sulfonated organosilicon compound. These difficultly-soluble sulfates can be precipitated, for example, by adding compounds of calcium, strontium or barium.

The resulting sulfonate solutions are transparent, e.g., colloidal, colorless to very pale yellow liquids having a density of about 1.0 to 1.3 g/l.

The invention will now be explained in detail with reference to the following examples. These Examples are intended to illustrate the invention and should not be construed as limiting the same.

EXAMPLE 1

1.5 kg (3.16 mol) of $S_2[(CH_2)_3Si(OC_2H_5)_3]_2$ was mixed with 1.5 liters of ethanol in a 10-liter glass flask equipped with a KPG agitator, dropping funnel and reflux condenser. The mixture was heated to 50° C. and mixed under agitation with 600 g of 0.1 N aqueous HCl solution. The solution, which was practically clear, immediately heated up to about 60° C. and gelled within 5 minutes. After 2 liters of water had been added, the suspension was agitated with reflux for 2 hours and then cooled to 50° C. The liquid phase was then separated via a dip tube and a screen device.

The remaining solid was washed four times, each time with 2 liters of water and then mixed with 1700 ml water and 800 g of 35% hydrogen peroxide solution. The suspension was first agitated at 40°–50° C. for 3 hours and then mixed with an additional 800 g of 35% hydrogen peroxide solution in 4 hours, then agitated at 60° C. for an additional 4 hours and then at about 100° C. for 4 hours. The solution, which was nearly transparent, was filtered off through a 2-liter Seitz pressure filter. The result was a 1.355 normal solution of Si-$(OH)_3$-$(CH_2)_3$-$SO_3H$. The oxidation yield was about 98% (relative to intermediately-formed polymeric disulfane).

EXAMPLE 2

200 grams (0.271 mol) of the $Si(OH)_3$-$(CH_2)_3$-$SO_3$-H-containing solution prepared as in Example 1 was mixed with 271 ml of 1 N NaOH solution under agitation in 5 minutes. The pH of the solution was then determined to be about 7. About 475 g of a solution containing a total of 271 mmol of $Si(OH)_3$-$(CH_2)_3$-$SO_3Na$ was obtained.

EXAMPLE 3

100 grams (0.203 mol) of $S_2[(CH_2)_3SiO_{3/2}]_2 \cdot 4SiO_2$ with an average particle size of 50 μm was suspended in 300 ml water. The suspension was heated to 70° C. and mixed with 98.6 g (1.015 mol) of 35% hydrogen peroxide solution with vigorous agitation for 10 hours. The suspension, which still contained a small amount of solid, was agitated at 100° C. for an additional 5 hours, then cooled and filtered. The solid component remaining on the filter (about 1 g of dry product) was washed twice with 50 ml of water each time.

After the filtrate and the washing liquor had been combined, the resulting solution was made up to 500 ml with water. Titration of this solution with 0.1 N NaOH solution gave a content of 0.78 mol/l of $2Si(OH)_4 \cdot Si(OH)_3$-$(CH_2)_3$-$SO_3H$. (Oxidation yield 96%).

20 ml of the resulting sulphonate solution was first concentrated to dryness in a drying cupboard. The remaining solid was finally dried at 150° C., and elementary analysis was made. The result of analysis relative to the now present organopolysiloxane, consisted of the following units:

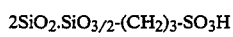

$2SiO_2 \cdot SiO_{3/2}$-$(CH_2)_3$-$SO_3H$ was as follows:

|  | % C | % H | % Si | % S |
| --- | --- | --- | --- | --- |
| Theoretical: | 12.2 | 7.1 | 28.5 | 10.9 |
| Found: | 11.6 | 7.9 | 27.6 | 10.2 |

In order to demonstrate the solubility of the resulting product, 20 ml water was added to the solid remaining after elementary analysis. After heating to 60° C. for 10 minutes, the solution again became clear.

EXAMPLE 4

1.0 liter of a solution containing about 0.6 mol/l of $Si(OH)_3$-$(CH_2)$-$SO_3H$ and about 0.6 mol/l of sulfuric acid was obtained, starting from 100 g (0.316 mol) of $S_4[(CH_2)_3SiO_{3/2}]_2$, by reaction with 338 g of 35% $H_2O_2$ solution as per Example 3 (oxidation yield about 95%).

The sulfuric acid formed in addition to the sulfonated organosilicon compound was quantitatively determined by ion chromatography.

EXAMPLE 5

100 g (0.302 mol) of

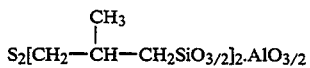

having an average particle size of 40 μm was suspended in 400 ml of water. The suspension was heated to 80° C. and 755 ml of a 2- molar aqueous solution of $H_2SO_5$ (Caro's acid) was added with vigorous agitation. The mixture was agitated at 100° C. for an additional 5 hours and then processed as in Example 3. The initially-obtained clear solution of product was concentrated to exactly 500 ml at 20 mbar and 80° C. It was shown by titration and ion chromatography that the resulting solution contained 1.15 mol/l of

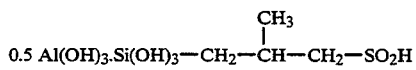

(oxidation yield: 95%).

EXAMPLE 6

50 grams (0.127 mol) of

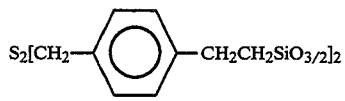

200 ml water was reacted as in Example 3 with 62 g (0.64 mol) of 35% hydrogen peroxide. During the reaction the pH of the suspension was kept in the range from 5 to 7 by pH-controlled metered addition of 0.1 N caustic soda solution.

The resulting solution was adjusted to exactly 1.0 liters. Elementary analysis of a concentrated, dried residue showed that the substance was a 0.233 molar solution of

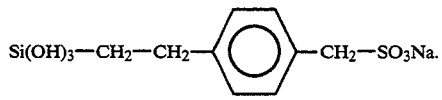

Oxidation yield: 92%.

Analysis of the dried product (see Example 3) relative to the following composition:

$SiO_{3/2}$—$CH_2CH_2$—⟨⟩—$CH_2SO_3Na$:

|  | % C | % H | % Si | % S | % Na |
|---|---|---|---|---|---|
| Theoretical: | 39.6 | 3.7 | 10.3 | 11.7 | 8.4 |
| Found: | 38.9 | 4.0 | 9.7 | 10.9 | 8.1 |

The foregoing examples are intended to illustrate the invention and not limit the same. Those skilled in the art will recognize that various changes and modifications can be made without departing from the spirit and scope of the invention.

The priority document, German Patent Application No. 41 42 129.9, filed in Germany on Dec. 20, 1991, is relied on and entirely incorporated herein by reference.

We claim:

1. A method of producing 0.01 to 70 wt. % aqueous solutions of sulfonated organosilicon compounds having a formula corresponding to formula (I):

or oligomeric siloxane derivatives thereof, condensed via oxygen bridges, wherein $R^1$ denotes a straight-chain or branched alkylene group with 1 to 12 carbon atoms, a cycloalkylene group with 5 to 8 carbon atoms or a unit having a formula corresponding to formula (II):

(II)

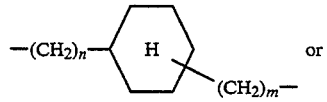

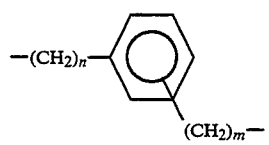

n or m is a number from 0 to 6 and denotes the number of methylene groups bound to the silicon or sulfur atom; wherein M from formula (I) denotes $H^+$, $NH_4^+$, or a metal ion having a valence of x, wherein x is 1 to 4, wherein the solution optionally also contains compounds having a formula corresponding to formula (III):

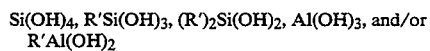

or derivatives thereof condensed via oxygen bridges, wherein R' denotes a methyl or ethyl group and a ratio of Si atoms from formula (I) to a sum of the Si and/or Al atoms from formula (III) is in the range of 1:0 to 1:3, and a total concentration of compounds of formula (I) and formula (III) is 0.01 to 70 wt. %, the method comprising:

suspending a polymeric disulfane, trisulfane or tetrasulfane compound in water, wherein the polymeric compound is made up of units having a formula corresponding to formula (IV):

wherein $R^1$ at each location in formula (IV) is the same or different and has the same meaning as in formula (I), y is 2, 3 or 4, and the free valences of oxygen atoms bonded to the silicon atom in formula (IV) are saturated by silicon atoms in other formula (IV) groups or by metal atom/oxygen groups in cross-linking bridge members corresponding to formula (V):

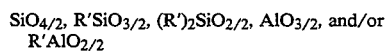

wherein R' in formula (V) has the same meaning as in formula (III), and a ratio of Si atoms from formula (IV)

units to a sum of Si and/or Al atoms from formula (V) units is 1:0 to 1:3, wherein the suspended compounds are present in the water at a concentration of 0.1 to 50 wt. %;

adding hydrogen peroxide to the suspension at a temperature in the range of 10° to 100° C. for 2 to 20 hours, wherein the hydrogen peroxide is added in a form of up to a 70 wt. % solution, and the quantity of hydrogen peroxide used is at least an amount stoichiometrically required for oxidizing the formula (IV) sulfane compound into the sulfone compound of formula (I);

agitating the suspension at a temperature in the range of 30° to 100° C. for up to 60 hours and at 100° to 150° C. for up to an additional 60 hours at a normal pressure or an excess pressure equal to a sum of the partial pressures of the components of the mixture at the respective temperature until a substantially clear solution has been obtained and any excess hydrogen peroxide present has decomposed;

cooling the solution and optionally neutralizing the solution;

separating any insoluble components present by filtering or centrifuging and washing with a washing liquid; and bringing the solution of product combined with the washing liquid to a desired concentration by diluting the solution with water or by concentrating the solution.

2. A method of producing aqueous solutions of sulfonated organosilicon compounds according to claim 1, wherein the compound of formula (I) is a compound as follows:

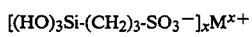
[(HO)$_3$Si-(CH$_2$)$_3$-SO$_3^-$]$_x$M$^{x+}$ or an oligomeric derivative thereof, wherein the polymeric disulfane, trisulfane or tetrasulfane compound of formula (IV) used as a starting material consists of units having a formula as follows:

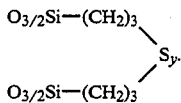

3. A method of producing aqueous solutions of sulfonated organosilicon compounds according to claim 1, wherein the compound of formula (IV) used as a starting material is a polymeric disulfane having a formula

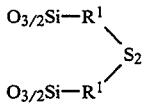

wherein R$^1$ has the same meaning as in formula (IV).

4. A method of producing aqueous solutions of sulfonated organosilicon compounds according to claim 1, wherein the compound of formula (I) is a compound as having a formula as follows:

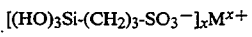
[(HO)$_3$Si-(CH$_2$)$_3$-SO$_3^-$]$_x$M$^{x+}$ wherein a polymeric disulfane having the formula

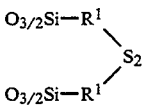

is used as the formula (IV) compound.

5. A method of producing aqueous solutions of sulfonated organosilicon compounds according to claim 1, wherein the compound of formula (IV) is suspended in water at a pH of 3 to 9.

6. A method of producing aqueous solutions of sulfonated organosilicon compounds according to claim 1, wherein M is a metal ion having a valence of x=1 to 4, wherein a pH of the suspension during oxidation is kept in the range from 3 to 9 by adding ammonia, amine, water-soluble metal oxide, water-soluble metal hydroxide, water-soluble metal hydrogen carbonate, water-soluble metal carbonate, or aqueous solutions thereof.

7. A method of producing aqueous solutions of sulfonated organosilicon compounds according to claim 1, wherein the compound of formula (IV) is suspended in water at a concentration of 10 to 35 wt. % before oxidation begins.

8. A method of producing aqueous solutions of sulfonated organosilicon compounds according to claim 1, wherein the compound of formula (IV) is oxidized with about 35 wt. % hydrogen peroxide.

9. A method of producing aqueous solutions of sulfonated organosilicon compounds according to claim 1, wherein the quantity of hydrogen peroxide used for oxidation is in a stoichiometric excess of up to 10 mol % relative to an amount needed to convert all the sulfur atoms in the compound of formula (IV) into sulfonate and optionally sulfate units.

10. A method of producing aqueous solutions of sulfonated organosilicon compounds according to claim 1, wherein the compound of formula (IV) is produced in situ and directly before oxidation thereof, wherein this in situ produced compound of formula (IV) is then washed to be freed from by-products produced during its production and then oxidized when wet or without a drying step.

11. A method of producing aqueous solutions of sulfonated organosilicon compounds according to claim 1, wherein after cooling, neutralization of the solution is performed, wherein the neutralization is performed with ammonia, an amine, a water-soluble metal oxide, a water-soluble metal hydroxide, a water soluble metal hydrogen carbonate, a water-soluble metal carbonate or aqueous solutions thereof.

12. A method of producing aqueous solutions of sulfonated organosilicon compounds according to claim 1, wherein the solution consists essentially of the sulfonated organosilicon compound of formula (I) and water.

13. A method of producing aqueous solutions of sulfonated organosilicon compounds according to claim 1, wherein water is the sole solvent present.

14. The use of the aqueous solutions of sulfonated organosilicon compounds according to claim 1 as starting materials for producing an insoluble acid catalyst, an ion exchanger or for surface modification of inorganic materials.

15. A method of producing 0.01 to 70 wt. % aqueous solutions of sulfonated organosilicon compounds having a formula corresponding to formula (I):

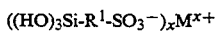

or oligomeric siloxane derivatives thereof, condensed via oxygen bridges, wherein $R^1$ denotes a straight-chain or branched alkylene group with 1 to 12 carbon atoms, a cycloalkylene group with 5 to 8 carbon atoms or a unit having a formula corresponding to formula (II):

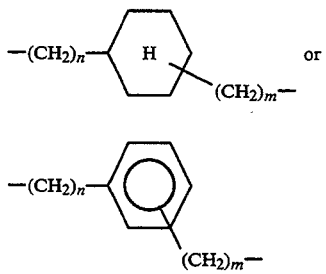
(II)

wherein n or m is a number from 0 to 6 and denotes the number of methylene groups bound to the silicon or sulfur atom; wherein M from formula (I) denotes $H^+$, $NH_4^+$, or a metal ion having a valence of x, wherein x is 1 to 4, wherein the solution optionally also contains compounds having a formula corresponding to formula (III):

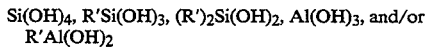
(III)

or derivatives thereof condensed via oxygen bridges, wherein R' denotes a methyl or ethyl group and a ratio of Si atoms from formula (I) to a sum of the Si and/or Al atoms from formula (III) is in the range of 1:0 to 1:3, and a total concentration of compounds of formula (I) and formula (III) is 0.01 to 70 wt. %, the method comprising:

suspending a polymeric disulfane, trisulfane or tetrasulfane compound in water, wherein the polymeric compound is made up of units having a formula corresponding to formula (IV):

(IV)

wherein $R^1$ at each location in formula (IV) is the same different and has the same meaning as in formula (I), y is 2, 3 or 4, and the free valences of oxygen atoms bonded to the silicon atom in formula (IV) are saturated by silicon atoms in other formula (IV) groups or by metal atom/oxygen groups in cross-linking bridge members corresponding to formula (V):

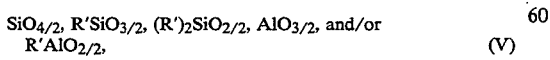
(V)

wherein R' in formula (V) has the same meaning as in formula (III), and a ratio of Si atoms from formula (IV) units to a sum of Si and/or Al atoms from formula (V) units is 1:0 to 1:3, wherein the suspended compounds are present in the water at a concentration of 0.1 to 50 wt. %;

adding an oxidizing agent to the suspension at a temperature in the range of 10° to 100° C. for 2 to 20 hours, wherein the oxidizing agent is an organic or inorganic peracid or bromine water, optionally formed in situ and optionally in salt form, wherein the quantity of the oxidizing agent used is at least an amount stoichiometrically required for oxidizing the formula (IV) sulfane compound into the sulfone compound of formula (I);

agitating the suspension at a temperature in the range of 30° to 100° C. for up to 60 hours and at 100° to 150° C. for up to an additional 60 hours at a normal pressure or an excess pressure equal to a sum of the partial pressures of the components of the mixture at the respective temperature until a substantially clear solution has been obtained and any excess oxidizing agent present has decomposed;

cooling the solution and optionally neutralizing the solution with ammonia, an amine, a water-soluble metal oxide, a water-soluble metal hydroxide, a water-soluble metal hydrogen carbonate, a water-soluble metal carbonate or aqueous solutions thereof;

separating any insoluble components present by filtering or centrifuging and washing with a washing liquid; and bringing the solution of product combined with the washing liquid to a desired concentration by diluting the solution with water or by concentrating the solution.

16. A method of producing 0.01 to 70 wt. % aqueous solutions of sulfonated organosilicon compounds having a formula corresponding to formula (I):

or oligomeric siloxane derivatives thereof, condensed via oxygen bridges, wherein $R^1$ denotes a straight-chain or branched alkylene group with 1 to 12 carbon atoms, a cycloalkylene group with 5 to 8 carbon atoms or a unit having a formula corresponding to formula (II):

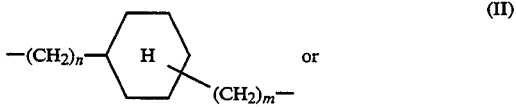
(II)

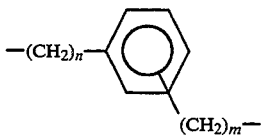

wherein n or m is a number from 0 to 6 and denotes the number of methylene groups bound to the silicon or sulfur atom; wherein M from formula (I) denotes $H^+$, $NH_4^+$, or a metal ion having a valence of x, wherein x is 1 to 4, wherein the solution optionally also contains compounds having a formula corresponding to formula (III):

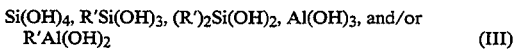
(III)

or derivatives thereof condensed via oxygen bridges, wherein R' denotes a methyl or ethyl group and a ratio of Si atoms from formula (I) to a sum of the Si and/or Al atoms from formula (III) is in the range of 1:0 to 1:3, and a total concentration of compounds of formula (I) and formula (III) is 0.01 to 70 wt. %, the method comprising:

suspending a polymeric disulfane, trisulfane or tetrasulfane compound in water, wherein the polymeric compound is made up of units having a formula corresponding to formula (IV):

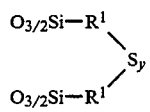
(IV)

wherein $R^1$ at each location in formula (IV) is the same or different and has the same meaning as in formula (I), y is 2, 3 or 4, and the free valences of oxygen atoms bonded to silicon atom in formula (IV) are saturated by silicon atoms in other formula (IV) groups or by metal atom/oxygen groups in cross-linking bridge members corresponding to formula (V):

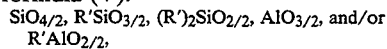
(V)

wherein R' in formula (V) has the same meaning as in formula (III), and a ratio of Si atoms from formula (IV) units to a sum of Si and/or Al atoms from formula (V) units is 1:0 to 1:3, wherein the suspended compounds are present in the water at a concentration of 0.1 to 50 wt. %;

adding an oxidizing agent to the suspension at a temperature in the range of 10° to 100° C. for 2 to 20 hours, wherein the oxidizing agent is an organic or inorganic peracid or bromine water, optionally formed in situ and optionally in salt form, wherein the quantity of the oxidizing agent used is at least an amount stoichiometrically required for oxidizing the formula (IV) sulfane compound into the sulfone compound of formula (I);

agitating the suspension at a temperature in the range of 30° to 100° C. for up to 60 hours and at 100° to 150° C. for up to an additional 60 hours at a normal pressure or an excess pressure equal to a sum of the partial pressures of the components of the mixture at the respective temperature until a substantially clear solution has been obtained;

cooling the solution and optionally neutralizing the solution with ammonia, an amine, a water-soluble metal oxide, a water-soluble metal hydroxide, a water-soluble metal hydrogen carbonate, a water-soluble metal carbonate or aqueous solutions thereof;

bringing the solution of product to a desired concentration by diluting the solution with water or by concentrating the solution.

17. The method according to claim 16, wherein the oxidizing agent is hydrogen peroxide.

* * * * *